United States Patent
Menzel

(10) Patent No.: US 9,591,997 B2
(45) Date of Patent: Mar. 14, 2017

(54) DEVICE, SYSTEM, AND METHOD FOR PATIENT ACTIVITY MONITORING

(71) Applicant: Mindray DS USA, Inc., Mahwah, NJ (US)

(72) Inventor: Frank Menzel, Oakland, NJ (US)

(73) Assignee: SHENZHEN MINDRAY BIO-MEDICAL ELECTRONICS CO. LTD., Shenzhen (CN)

(*) Notice: Subject to any disclaimer, the term of this patent is extended or adjusted under 35 U.S.C. 154(b) by 85 days.

(21) Appl. No.: 14/466,704

(22) Filed: Aug. 22, 2014

(65) Prior Publication Data
US 2016/0051166 A1 Feb. 25, 2016

(51) Int. Cl.
| | | |
|---|---|---|
| G06F 19/00 | (2011.01) | |
| A61B 5/00 | (2006.01) | |
| A61B 5/11 | (2006.01) | |
| A61B 5/0402 | (2006.01) | |
| A61B 5/1455 | (2006.01) | |

(52) U.S. Cl.
CPC ........... *A61B 5/1118* (2013.01); *A61B 5/002* (2013.01); *A61B 5/1116* (2013.01); *A61B 5/1123* (2013.01); *A61B 5/7246* (2013.01); *A61B 5/7264* (2013.01); *A61B 5/7282* (2013.01); *A61B 5/746* (2013.01); *G06F 19/345* (2013.01); *G06F 19/3431* (2013.01); *A61B 5/0402* (2013.01); *A61B 5/1455* (2013.01)

(58) Field of Classification Search
None
See application file for complete search history.

(56) References Cited

U.S. PATENT DOCUMENTS

| | | | | |
|---|---|---|---|---|
| 6,165,143 | A * | 12/2000 | van Lummel | 600/595 |
| 6,997,882 | B1 * | 2/2006 | Parker | A61B 5/08 600/301 |
| 8,905,948 | B2 * | 12/2014 | Davis et al. | 600/595 |
| 2005/0033200 | A1 * | 2/2005 | Soehren | A61B 5/0002 600/595 |
| 2007/0038155 | A1 * | 2/2007 | Kelly et al. | 600/595 |
| 2007/0129769 | A1 * | 6/2007 | Bourget et al. | 607/45 |
| 2007/0159332 | A1 * | 7/2007 | Koblasz | 340/572.1 |
| 2008/0288200 | A1 * | 11/2008 | Noble | A61B 5/1116 702/96 |
| 2010/0262045 | A1 * | 10/2010 | Heaton et al. | 600/595 |
| 2010/0298742 | A1 * | 11/2010 | Perlman et al. | 600/595 |
| 2011/0231101 | A1 * | 9/2011 | Bidargaddi et al. | 702/19 |

(Continued)

*Primary Examiner* — William Thomson
*Assistant Examiner* — Davin Sands
(74) *Attorney, Agent, or Firm* — Kory D. Christensen; Stoel Rives LLP

(57) ABSTRACT

A portable telemetry device includes a physiological component, a movement component, a wireless radio, and a communication component. The physiological component is configured to receive, from at least one sensor, physiological data representative of a physiological condition of a patient. The movement component is configured to detect movement of the portable telemetry device and generate movement data. The portable telemetry device is configured to attach to the patient. The wireless radio is configured to wirelessly send radio signals. The communication component is configured to transmit the physiological data and the movement data to a monitoring system using the wireless radio.

15 Claims, 3 Drawing Sheets

(56) References Cited

U.S. PATENT DOCUMENTS

2011/0288379 A1* 11/2011 Wu .................... A61B 5/02
                                                600/301
2012/0059230 A1* 3/2012 Teller et al. ............. 600/301
2013/0060303 A1* 3/2013 Davis .................. A61B 5/4815
                                                607/59

* cited by examiner

DEVICE, SYSTEM, AND METHOD FOR PATIENT ACTIVITY MONITORING

TECHNICAL FIELD

The present disclosure relates to medical monitoring and more particularly relates to systems, methods, and devices for patient activity monitoring.

DETAILED DESCRIPTION OF PREFERRED EMBODIMENTS

Figure 1:
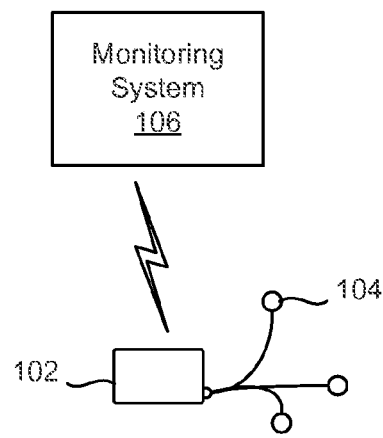
FIG. 1 is a schematic block diagram illustrating a telemetry system, according to one embodiment.

Modern medical practice makes extensive use of electronic monitoring of vital signs and other physiological parameters of patients. In some cases, remote monitoring of physiological parameters, or telemetry, is used to allow nurses, doctors, and/or computing devices to determine the health of a patient or detect problems with the patient when the nurse, doctor, or other medical worker is not physically present with the patient. In some cases, wireless telemetry devices worn by a patient may allow the patient to move around and/or be easily moved between locations while maintaining monitoring of the patient's vital signs. One example of a portable telemetry device is the Mindray Telepack®.

One aspect of patient health that may be of importance to medical workers is how much the patient moves or ambulates. For example, bed-ridden patients may need to be periodically moved or rolled over to reposition the patient and reduce the formation of bed sores. Similarly, periodic ambulation, or walking, may be good for the mental and physical health of a patient. In some situations, patients should not leave their bed, without assistance, due to weakness and/or likelihood of falling. However, tracking patient activity or movement is not available using current telemetry devices and systems. Rather, nurses, or other medical workers, are required to either physically monitor the patient or ask the patient questions to determine how much the patient has been moving. Interviewing patients can be time-consuming and subject to error.

In light of the foregoing, Applicants disclose devices, systems, and methods for monitoring physical activity or movement of a patient. In one embodiment, a portable telemetry device includes a physiological component, a movement component, a wireless radio, and a communication component. The physiological component is configured to receive, from at least one sensor, physiological data representative of a physiological condition of a patient. The movement component is configured to detect movement of the portable telemetry device and generate movement data.

In one embodiment, the portable telemetry device is configured to attach to the patient. The wireless radio is configured to wirelessly send radio signals. The communication component is configured to transmit the physiological data and the movement data to a monitoring system using the wireless radio.

In one embodiment, the portable telemetry device may detect an activity level of the patient, e.g., how much the patient moves within a period of time. In one embodiment, the portable telemetry device may identify a movement activity. For example, the portable telemetry device may determine that a patient has moved from a lying or sitting position to a standing position. Other movement activities may also be identified including sitting, walking, rolling over, or the like. In one embodiment, an alarm may be triggered in response to the detection of an event. In one embodiment, identifying movement activities and/or triggering alarms may be performed locally at the portable telemetry device or by a remote monitoring system.

Turning to the figures, FIG. 1 is a schematic diagram illustrating a monitoring system 106 and a portable telemetry device 102 for medical telemetry. In one embodiment, the portable telemetry device 102 includes a telemetry device worn by a patient. For example, the patient may be free to walk or move while wearing the portable telemetry device 102 due to size, weight, and/or capability for wireless communication.

The portable telemetry device 102 may include a portable device comprising a housing containing a processor, circuitry, computer readable memory, an antenna, radios, and/or the like. The portable telemetry device 102 may have a size such that it can be worn by a patient while allowing the patient to move freely. The portable telemetry device 102 may include one or more ports for coupling to sensors and receiving signals from the sensors. The portable telemetry device 102 may include a human-machine interface, which may include a display, one or more buttons, and/or indicator lights to allow a human to determine a status of the portable telemetry device 102, enter information, or otherwise interact with the portable telemetry device 102.

The portable telemetry device 102 is in wireless communication with the monitoring system 106. Connected to the portable telemetry device 102 are a plurality of sensors 104 which may be used to measure patient parameters and/or obtain patient waveforms. For example, the sensors 104 may include one or more electrocardiography (ECG) sensors, a pulse oximetry sensor (e.g., $SpO_2$), and/or any other sensors. The portable telemetry device 102 may receive signals from the sensors 104 as analog or digital data signals indicating a physiological condition of a patient. The portable telemetry device 102 may also obtain movement data from a movement sensor connected to the portable telemetry device 102 or integrated within the housing of the portable telemetry device 102. In one embodiment, the portable telemetry device 102 may send physiological parameters and movement data to the monitoring system 106. For example, the portable telemetry device 102 may forward processed or unprocessed sensor data to the monitoring system 106 so that a doctor, a nurse, and/or other medical personnel can monitor a condition of the patient.

The monitoring system 106 may include a computing device such as a computer, a server, or the like. The monitoring system 106 may include a processor, circuitry, computer readable memory, an antenna, radios, communication ports, and/or the like. In one embodiment, the monitoring system 106 includes a computing system. For example, the monitoring system 106 may include a computing system for a nursing station, an intensive care ward, a step down ward, and/or an in-patient ward.

The monitoring system 106 receives the physiological data and movement data from the portable telemetry device 102 and stores and/or processes the data. In one embodiment, the monitoring system 106 stores the physiological data and movement data in memory for later access and/or analysis. In one embodiment, the monitoring system 106 processes the physiological data and/or movement data to detect problems in relation to the patient, detect whether there is an alarm condition, or perform other analysis. For example, the monitoring system 106 may report an alarm condition to a nurse, a doctor, or other medical personnel.

The monitoring system 106 may also provide control data to the portable telemetry device 102 to configure alarm settings, reset alarms, determine a state or location of the portable telemetry device 102, transfer stored data, or otherwise configure operation of the portable telemetry device 102. In one embodiment, the monitoring system 106 may send and receive control data between the portable telemetry device 102 to determine that messages were received or that instructions corresponding to control data were performed.

Figure 2:
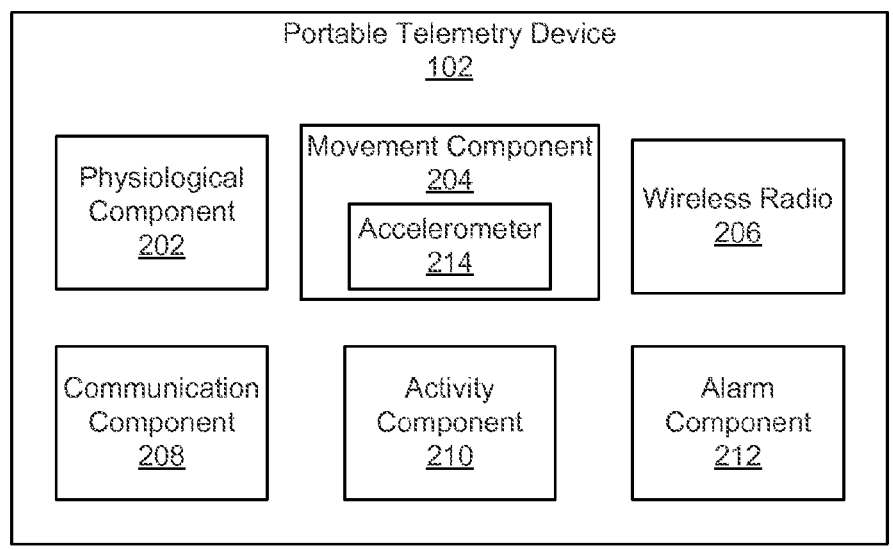
FIG. 2 is a schematic block diagram illustrating a portable telemetry device, according to one embodiment.

FIG. 2 is a schematic block diagram illustrating components of a portable telemetry device 102, according to one embodiment. The portable telemetry device 102 includes a physiological component 202, a movement component 204, a wireless radio 206, a communication component 208, an activity component 210, and an alarm component 212. The components 202-212 are given by way of example only and may not all be included in all embodiments. In some embodiments, one or more of the components 202-212 may be located in a remote monitoring system 106. For example, the monitoring system 106 may include the activity component 210 and/or the alarm component 212 and may process any movement data received from the portable telemetry device 102.

The physiological component 202 is configured to receive physiological data of a patient. The physiological data may be based on signals or data received from one or more sensors 104 in communication with the portable telemetry device 102. For example, the physiological component 202 may receive signals or data from the one or more sensors 104 of FIG. 1 that are connected to the portable telemetry device 102. The physiological data may include ECG data, SpO$_2$ data, or any other type of data representative of a physiological condition of the patient.

The movement component 204 is configured to detect movement of the patient. In one embodiment, the movement component 204 may detect movement of the patient by detecting movement of the portable telemetry device 102. For example, the portable telemetry device 102 may be connected or attached to a patient so that when the patient moves, the portable telemetry device 102 moves with the patient. In one embodiment, the movement component 204 includes an accelerometer 214, such as a three-axis accelerometer. The accelerometer 214 may be mounted within a housing of the portable telemetry device 102. The accelerometer 214 may produce one or more electrical signals to indicate movements, rotations, and/or accelerations of the portable telemetry device 102.

The wireless radio 206 may include a radio that is configured to communicate wirelessly using radio signals. The wireless radio 206 may be configured to operate according to a wireless standard. Example wireless standards include an institute for electrical and electronics engineers (IEEE) 802.11 standard (known to industry groups as Wi-Fi), a cellular communication standard (such as 3GPP LTE), a Bluetooth standard, or another standard. Similarly, the wireless radio 206 may be configured to operate within a licensed or unlicensed band. One example of licensed bands in the United States includes the wireless medical telemetry service (WMTS) bands which include dedicated protected bands which have been allocated for medical telemetry purposes. One example of unlicensed bands includes the widely used industrial, scientific, and medical (ISM) radio bands. The frequency band and standard may vary considerably and may allow the portable telemetry device 102 to communicate with a monitoring system 106.

The communication component 208 is configured to communicate data with the monitoring system 106. For example, the communication component 208 may transmit the physiological data from the physiological component 202 and the movement data from the movement component 204 to a monitoring system 106 using the wireless radio 206. In one embodiment, the communication component 208 transmits physiological data or movement data that has been generated by the physiological component 202 or movement component 204. For example, signals from a sensor 104 or an accelerometer 214 may be converted to a digital format or other format that can be understood and processed by the monitoring system 106. In one embodiment, some data may be transmitted in a raw format (e.g., analog or sampled format) to be processed by the monitoring system 106.

The communication component 208 may also communicate other types of data such as alarm data or control data. In one embodiment, the movement component 204 may receive control data to configure operation of the portable telemetry device 102. For example, the control data may indicate that certain types of parameters are to be gathered and sent or that certain types of parameters are no longer needed. In one embodiment, the communication component 208 may receive information that indicates a threshold level for an alarm or a type of event or movement activity that should trigger an alarm. In one embodiment, the communication component 204 may transmit an indication that an alarm condition has been detected.

The activity component 210 is configured to detect or identify a movement activity based on movement data from the movement component 204. In one embodiment, the activity component 210 detects movement activities performed by the patient based on movement detected by the movement component 204. For example, the activity component 210 may process one or more output sensors from an accelerometer 214 to identify what a patient is doing. Different movements have different signatures which can be detected. In one embodiment, the activity component 210 may detect an activity movement including information about a current static position of a patient. For example, if a three-axis accelerometer is used an orientation of the portable telemetry device 102 can be determined and a corresponding position of the patient may be detected. For example, the activity component 210 may determine whether the patient is standing, in a reclined seated position, or lying down. As another example, the activity component 210 may determine whether the patient is moving or resting (mostly stationary except for breathing or other minor muscle movements producing movement data below a threshold).

In one embodiment, the activity component 210 may detect a movement activity that involves physical movement. For example, the movement activity may detect a waveform signature from an accelerometer 214 corresponding to the patient standing up, sitting down, walking, or the like. In one embodiment, the activity component 210 may detect a patient standing up from a sitting or lying position by detecting a rest position and a short upward acceleration followed by a slowing and stop in the upward acceleration. In one embodiment, the activity component 210 may detect a patient walking by detecting periodic up/down accelerations corresponding to steps of the patient. In one embodiment, the activity component 210 may detect the patient sitting down by detecting a rest followed by a short downward acceleration and then a stop in the downward acceleration. In one embodiment, the activity component 210 may detect the patient rolling over by detecting a rolling of the portable telemetry device 102. For example, the portable patient monitor may have little horizontal movement along one axis while rolling about that axis. One of skill in the art will recognize, in light of the present disclosure, considerable variation in how different movement activities of the patient may be detected.

In one embodiment, the activity component 210 may determine an activity level of the patient. For example, the activity component 210 may count a number of movements of the patient per minute that exceeded a movement threshold. This activity level may be provided to a medical worker who can see a most current activity level or review the activity level of the patient over time.

In one embodiment, the activity component 210 may compare the movement data with data from one or more sensors 104 to determine the movement activity. For example, an ECG signal may show that a patient is currently physically exerting himself or herself while the movement data indicates that the patient is rolling over. The activity component 210 may be able to determine that the physiological data and movement data corresponds to each other and indicates that the patient is rolling himself or herself over in bed. Similar other correlations may be used to reduce false positive detections of movements or confirm the occurrence of a movement.

The alarm component 212 is configured to provide an alarm in response to an alarm condition. In one embodiment, the alarm component 212 provides an alarm in response to a movement activity. For example, an alarm condition may be set up to trigger an alarm in response to detection of a movement activity detected by the activity component 210. In one embodiment, an alarm may be triggered in response to a patient standing up. For example, there are some situations where patients are too unhealthy to stand or walk on their own. In these situations, an alarm may be configured to notify a nurse or other medical worker if the patient stands or is attempting to stand. Thus, medical personnel can quickly go assist the patient before any fall or injury is sustained.

Figure 3:
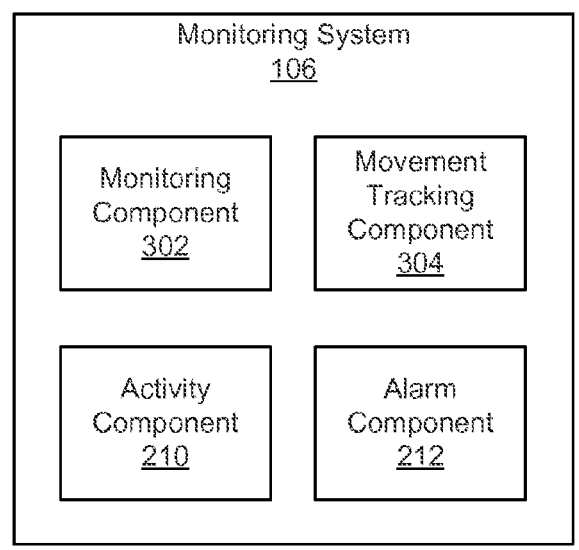
FIG. 3 is a schematic block diagram illustrating components of a monitoring system, according to one embodiment.

FIG. 3 is a schematic block diagram illustrating components included in a monitoring system 106, according to one embodiment. The monitoring system 106 includes a monitoring component 302 and a movement tracking component 304. The monitoring system 106 may also include an activity component 210 and an alarm component 212. The components 302-304 and 210-212 are given by way of example only and may not all be included in all embodiments.

The monitoring component 302 is configured to receive data from the portable telemetry device 102. The monitoring component 302 may also store or evaluate the data. In one embodiment, the monitoring component 302 processes physiological parameters to detect alarm conditions or a health status of one or more patients with one or more corresponding portable telemetry devices 102. For example, a nurse or other medical worker may be able to remotely monitor the patient's physiological status by viewing sensor data for the patient. The monitoring component 302 may also receive movement data for processing or storage, or may provide the movement data to the movement tracking component 304, activity component 210, or alarm component 212.

The movement tracking component 304 is configured to track movement activities of one or more patients over time. In one embodiment, the movement tracking component 304 may generate reports indicating movement activity of a patient. For example, the movement tracking component 304 may generate statistical data or information indicating how much a patient has moved or performed specific movement activities during a time period based on information provided by the portable telemetry device 102. In one embodiment, the movement tracking component 304 tracks a number of occurrences of a movement activity over a specific time period. For example, the movement tracking component 304 may determine that a patient has rolled over in bed a specific number of times during the night. In one embodiment, the movement tracking component 304 tracks a percentage of time or total number of hours during which a patient is moving or walking. For example, the movement tracking component 304 may determine a percentage of time during the day that the patient spends walking. Similarly, the movement tracking component 304 may track a percentage of time or total number of hours during which the patient is resting or lying down. In one embodiment, the movement tracking component 304 may determine how long it has been since a patient went on a walked or rolled over in bed. If the patient hasn't walked or rolled over in bed for a threshold amount of time, a nurse or other medical worker may be dispatched to help the patient.

The movement tracking component 304 may generate information to log the occurrence of any movement activities. For example, the activity component 210, of the portable telemetry device 102 or monitoring system 106, may detect a movement activity and the movement tracking component 304 may log a date, time, location, or other information corresponding to the occurrence of the movement activity. A nurse, a doctor, or other medical worker may later review the information to determine how active the patient is. The movement tracking component 304 may tag a portion of the movement data (e.g., accelerometer output data) with the corresponding activity movement log data. Thus, a medical worker may be able to come along later to review the data and what occurred with the patient.

Figure 4:
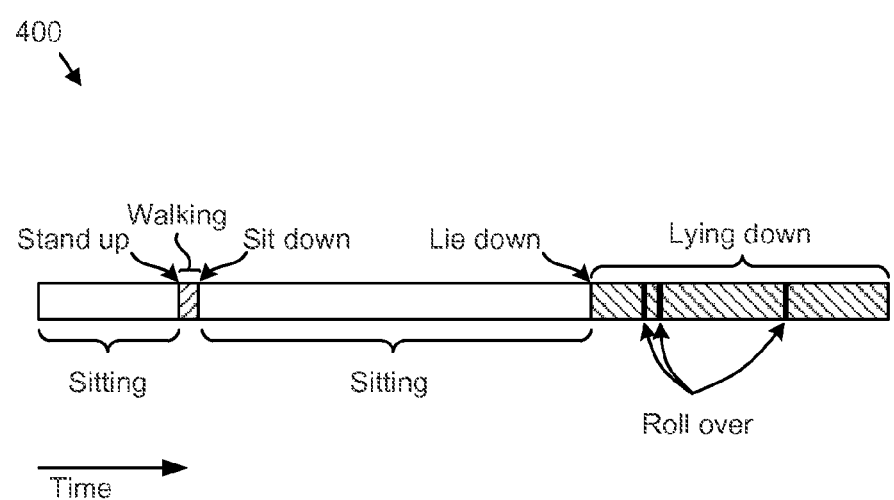
FIG. 4 is a schematic diagram illustrating a patient's movement activity over time, according to one embodiment.

FIG. 4 is a schematic diagram 400 illustrating a patient's movement activity over time. In one embodiment, the diagram 400, or similar information, may be viewed by a nurse or other medical worker to determine an activity level of a patient. The nurse or medical worker may take steps to assist the patient roll over, take a walk, or perform other movements, if needed. In the diagram 400, the patient is initially sitting. The patient stands up and spends a period of time walking and then sits down once more. After sitting for a period of time, the patient lies down and rolls over a few times while lying down. In one embodiment, as the patient, with an attached portable telemetry device 102, performs the movements illustrated in the diagram 400, the movement tracking component 304 may track the movements and create a log or report, or otherwise store information regarding the movements for later review by a medical worker or the monitoring system 106.

Returning to FIG. 3, the monitoring system 106 may also include an activity component 210 and alarm component 212. The activity component 210 and alarm component 212 may include any of the functionality or features as discussed above in relation to the portable telemetry device 102. For example, the functionality of the activity component 210 and alarm component 212 may be performed at the monitoring system 106 instead of at the portable telemetry device 102.

Figures 5, 6:
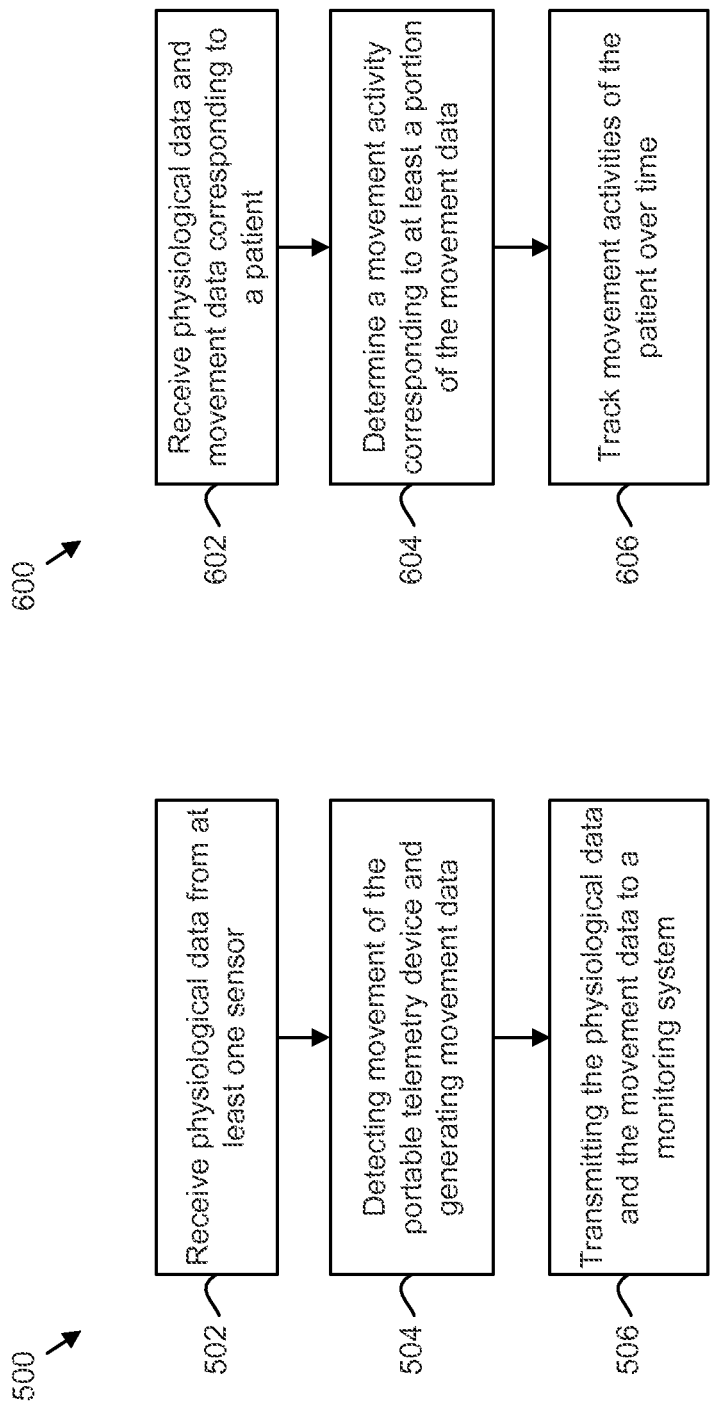
FIG. 5 is a schematic flow chart diagram illustrating a method for monitoring patient activity, according to one embodiment.
FIG. 6 is a schematic flow chart diagram illustrating another method for monitoring patient activity, according to one embodiment.

FIG. 5 is a schematic flow chart diagram illustrating a method 500 for tracking physical activity of a patient, according to one embodiment. In one embodiment, the method 500 is performed by a portable telemetry device 102, such as the portable telemetry device 102 of FIG. 2.

The method 500 begins and a physiological component 202 receives 502 physiological data representative of a physiological condition of a patient. For example, the portable telemetry device 102 may be connected to one or more sensors 104, such as ECG or $SpO_2$ sensors, to monitor a physiological condition of the patient. The physiological component 202 may receive 502 the physiological data in digital or analog format from the sensors 104.

A movement component 204 detects 504 movement of the portable telemetry device 102 and generates movement data. The movement data may include sensor data or a waveform from an accelerometer 214 or other sensor that can detect physical movement. In one embodiment, portable telemetry device 102 is configured to attach to the patient so that the movement data also corresponds to the patient. In one embodiment, the portable telemetry device 102 is attached to the patient such that the portable telemetry device 102 rotates, tilts, and moves with the patient.

A communication component 208 transmits 506 the physiological data and the movement data to a monitoring system 106 using a wireless radio 206. For example, the monitoring system 106 may monitor the physiological parameters and movement data to allow a nurse or other medical worker to track movement of the patient as well as monitor a physiological condition. Thus, a medical worker may be able to determine what needs a patient has for physical activity, movement, or repositioning based on how active the patient has been.

FIG. 6 is a schematic flow chart diagram illustrating a method 600 for tracking activity of a patient, according to one embodiment. The method 600 may be performed by a monitoring system 106, such as the monitoring system 106 of FIG. 3.

The method 600 begins and a monitoring component 302 receives 602 physiological data representative of a physiological condition of a patient and movement data corresponding to movements of the patient. For example, the monitoring component 302 may receive 602 the physiological data and movement data from one or more portable telemetry devices 102 which are used to monitor one or more corresponding patients.

An activity component 210 determines 604 a movement activity corresponding to at least a portion of the movement data. The activity component 210 may determine 604 the movement activity based on a waveform signature generated by an accelerometer 214, such as a three-axis accelerometer of a portable telemetry device 102. The activity component 210 may identify a specific activity and associate the specific activity with the movement data. In one embodiment, the activity component 210 may determine 604 whether a patient was assisted or unassisted during an activity. For example, the activity component 210 may determine 604 whether a nurse was with the patient when the patient rolled over. In one embodiment, a nurse may select an option on the portable telemetry device 102 to indicate that the nurse is present so that the activity component 210 can determine that movement activities were assisted.

A movement tracking component 304 tracks 606 movement activities of the patient over time. For example, the movement tracking component 304 may track 606 how many movement activities of a certain type are performed or may track 606 an activity level of a patient. In one embodiment, the movement tracking component 304 tracks 606 the time since a specific movement activity has occurred. For example, the movement tracking component 304 may track 606 how long it has been since a patient has rolled over, gone on a walk, or the like. The movement tracking component 304 may provide information regarding tracked activities to a medical worker.

Various techniques, or certain aspects or portions thereof, may take the form of program code (i.e., instructions) embodied in tangible media, such as floppy diskettes, CD-ROMs, hard drives, a non-transitory computer readable storage medium, or any other machine-readable storage medium, wherein when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, an EPROM, a flash drive, an optical drive, a magnetic hard drive, or another medium for storing electronic data. The eNB (or other base station) and UE (or other mobile station) may also include a transceiver component, a counter component, a processing component, and/or a clock component or timer component. One or more programs that may implement or utilize the various techniques described herein may use an application programming interface (API), reusable controls, and the like. Such programs may be implemented in a high-level procedural or an object-oriented programming language to communicate with a computer system. However, the program(s) may be implemented in assembly or machine language, if desired. In any case, the language may be a compiled or an interpreted language, and combined with hardware implementations.

It should be understood that many of the functional units described in this specification may be implemented as one or more components, which is a term used to more particularly emphasize their implementation independence. For example, a component may be implemented as a hardware circuit comprising custom very large scale integration (VLSI) circuits or gate arrays, off-the-shelf semiconductors such as logic chips, transistors, or other discrete components. A component may also be implemented in programmable hardware devices such as field programmable gate arrays, programmable array logic, programmable logic devices, or the like.

Components may also be implemented in software for execution by various types of processors. An identified component of executable code may, for instance, comprise one or more physical or logical blocks of computer instructions, which may, for instance, be organized as an object, a procedure, or a function. Nevertheless, the executables of an identified component need not be physically located together, but may comprise disparate instructions stored in different locations that, when joined logically together, comprise the component and achieve the stated purpose for the component.

Indeed, a component of executable code may be a single instruction, or many instructions, and may even be distributed over several different code segments, among different programs, and across several memory devices. Similarly, operational data may be identified and illustrated herein within components, and may be embodied in any suitable form and organized within any suitable type of data structure. The operational data may be collected as a single data set, or may be distributed over different locations including over different storage devices, and may exist, at least partially, merely as electronic signals on a system or network. The components may be passive or active, including agents operable to perform desired functions.

Reference throughout this specification to "an example" means that a particular feature, structure, or characteristic described in connection with the example is included in at least one embodiment of the present invention. Thus, appearances of the phrase "in an example" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on its presentation in a common group without indications to the contrary. In addition, various embodiments and examples of the present invention may be referred to herein along with alternatives for the various components thereof. It is understood that such embodiments, examples, and alternatives are not to be construed as de facto equivalents of one another, but are to be considered as separate and autonomous representations of the present invention.

It will be obvious to those having skill in the art that many changes may be made to the details of the above-described embodiments without departing from the underlying principles of the invention. The scope of the present invention should, therefore, be determined only by the following claims.

The invention claimed is:

1. A portable telemetry device comprising:
   a physiological component configured to receive, from at least one sensor, physiological data representative of a physiological condition of a patient;
   a movement component configured to detect multi-axis accelerations of the portable telemetry device and generate movement data, including multi-axis acceleration data, wherein the portable telemetry device is configured to attach to the patient;
   an activity component configured to distinguish between and identify each of a plurality of patient movement activities by:
      comparing a time-varying acceleration waveform pattern of the multi-axis acceleration data for a first time period with predetermined acceleration patterns to identify a first activity of the patient,
      identifying a transition movement by the patient from the first activity to a second activity based on a comparison of the time-varying acceleration waveform pattern with the predetermined acceleration patterns during a second time period,
      comparing a time-varying acceleration waveform pattern of the multi-axis acceleration data for a third time period with the predetermined acceleration patterns to identify the second activity of the patient;
   a wireless radio configured to wirelessly send radio signals; and
   a communication component configured to transmit a patient alert to a third party monitoring system with the physiological data and the movement data using the wireless radio, the patient alert including:
      an identification and duration of the first activity of the patient,
      identification of the transition movement to the second activity, and
      identification of the second activity of the patient.

2. The portable telemetry device of claim 1, further comprising an activity component configured to identify at least one of the movement activities corresponding to at least a portion of the multi-axis acceleration data.

3. The portable telemetry device of claim 2, wherein the activity component is configured to identify the multi-axis acceleration activity as one of the patient moving and the patient resting.

4. The portable telemetry device of claim 3, wherein the activity component is configured to identify the movement activity as the patient rolling over.

5. The portable telemetry device of claim 3, further comprising an alarm component configured to provide an alarm in response to detecting an occurrence of a specific movement activity.

6. The portable telemetry device of claim 3, wherein the activity component identifies the movement activity based on a signature in a waveform generated by an accelerometer.

7. A system comprising:
   a monitoring component configured to receive physiological data representative of a physiological condition of a patient and multi-axis acceleration data corresponding to movements of the patient;
   an activity component configured to distinguish between and identify each of a plurality of patient movement activities by:
      comparing a time-varying acceleration waveform pattern of the multi-axis acceleration data for a first time period with predetermined acceleration patterns to identify a first activity of the patient,
      identifying a transition movement by the patient from the first activity to a second activity based on a comparison of the time-varying acceleration waveform pattern with the predetermined acceleration patterns during a second time period,
   comparing a time-varying acceleration waveform pattern of the multi-axis acceleration data for a third time period with the predetermined acceleration patterns to identify the second activity of the patient;
   a movement tracking component configured to track the patient movement activities over time; and
   a third party alert system to notify a third party of:
      an identification and duration of the first activity of the patient,
      identification of the transition movement to the second activity, and
      identification of the second activity of the patient.

8. The system of claim 7, wherein the movement tracking component tracks a number of occurrences of the movement activity over a specific time period.

9. The system of claim 7, wherein the activity component is configured to identify the movement activity as one or more of the patient standing up and the patient sitting down.

10. The system of claim 7, wherein the activity component is configured to identify the movement activity as one or more of the patient walking and the patient rolling over.

11. The system of claim 7, wherein the movement tracking component tracks a percentage of the time during which a patient is one or more of moving and walking.

12. The system of claim 7, wherein the movement tracking component tracks a percentage of the time during which a patient is one or more of resting and lying down.

13. The system of claim 7, further comprising an alarm component configured to notify a medical worker in response to detecting a movement activity.

14. The system of claim 13, where the movement activity comprises standing up and wherein the alarm component is configured to notify the medical worker in response to the patient standing up.

15. The system of claim 7, wherein the activity component is configured to compare the movement data to patient data to determine the movement activity.

* * * * *